US008697722B2

(12) United States Patent
Jiang et al.

(10) Patent No.: US 8,697,722 B2
(45) Date of Patent: Apr. 15, 2014

(54) NICOTINIC ACETYLCHOLINE RECEPTOR MODULATORS

(75) Inventors: Faming Jiang, Mountain View, CA (US); Taline Khroyan, San Jose, CA (US); Cris M. Olsen, Soquel, CA (US); Willma E. Polgar, Sunnyvale, CA (US); Lawrence R. Toll, Redwood City, CA (US); Nurulain T. Zaveri, Saratoga, CA (US)

(73) Assignee: SRI International, Menlo Park, CA (US)

( * ) Notice: Subject to any disclaimer, the term of this patent is extended or adjusted under 35 U.S.C. 154(b) by 1176 days.

(21) Appl. No.: 11/934,583

(22) Filed: Nov. 2, 2007

(65) Prior Publication Data

US 2009/0118326 A1      May 7, 2009

(51) Int. Cl.
*A61K 31/439* (2006.01)
*C07D 453/00* (2006.01)

(52) U.S. Cl.
USPC ......... 514/305; 514/343; 546/133; 546/276.7

(58) Field of Classification Search
CPC .. C07D 401/12; C07D 401/04; C07D 487/04; C07D 451/14; C07D 453/02; C07D 451/04; C07D 453/04; A61K 31/493
USPC .................. 514/305, 343; 546/133, 276.7
See application file for complete search history.

(56) References Cited

U.S. PATENT DOCUMENTS

| | | | |
|---|---|---|---|
| 4,835,162 A | 5/1989 | Abood | |
| 4,920,127 A | 4/1990 | King et al. | |
| 4,959,367 A | 9/1990 | King | |
| 5,039,680 A | 8/1991 | Imperato et al. | |
| 5,096,901 A | 3/1992 | Ward et al. | |
| 5,198,447 A | 3/1993 | Tyers | |
| 5,200,413 A | 4/1993 | King et al. | |
| 5,223,511 A | 6/1993 | Turconi et al. | |
| 5,248,684 A | 9/1993 | Suzuki et al. | |
| 5,280,028 A | 1/1994 | Flynn et al. | |
| 5,399,562 A | 3/1995 | Becker et al. | |
| 5,446,050 A | 8/1995 | Rosen | |
| 5,468,758 A | 11/1995 | Cereda et al. | |
| 5,491,148 A | 2/1996 | Berger et al. | |
| 5,637,596 A | 6/1997 | Varasi et al. | |
| 6,077,846 A | 6/2000 | Qian et al. | |
| 6,117,889 A | 9/2000 | Shen et al. | |
| 6,392,045 B1 * | 5/2002 | Peters et al. | 546/125 |
| 6,413,978 B1 | 7/2002 | Makovec et al. | |
| 6,495,605 B2 | 12/2002 | McCullough et al. | |
| 6,541,478 B1 | 4/2003 | O'Malley et al. | |
| 6,828,330 B2 | 12/2004 | Walker et al. | |
| 6,849,620 B2 | 2/2005 | Walker et al. | |
| 6,852,716 B2 | 2/2005 | Walker et al. | |
| 6,858,613 B2 | 2/2005 | Rogers et al. | |
| 6,894,042 B2 | 5/2005 | Walker et al. | |
| 6,897,219 B2 | 5/2005 | Peters et al. | |
| 6,911,543 B2 | 6/2005 | Walker et al. | |
| 6,919,359 B2 | 7/2005 | Piotrowski et al. | |
| 6,951,849 B2 | 10/2005 | Kelly et al. | |
| 6,951,868 B2 | 10/2005 | Walker et al. | |
| 6,964,972 B2 | 11/2005 | Peters et al. | |
| 2002/0042426 A1 | 4/2002 | Makovec et al. | |
| 2003/0045540 A1 | 3/2003 | Wishka et al. | |
| 2003/0105089 A1 | 6/2003 | Wishka et al. | |
| 2004/0147522 A1 | 7/2004 | Wong et al. | |
| 2004/0157878 A1 | 8/2004 | Rogers et al. | |
| 2005/0176754 A1 | 8/2005 | Xie et al. | |
| 2005/0222196 A1 | 10/2005 | Walker et al. | |
| 2005/0228023 A1 | 10/2005 | Zaveri et al. | |
| 2005/0234092 A1 | 10/2005 | Walker et al. | |
| 2005/0250808 A1 | 11/2005 | Xie et al. | |
| 2005/0282823 A1 | 12/2005 | Breining et al. | |

FOREIGN PATENT DOCUMENTS

| | | | |
|---|---|---|---|
| WO | WO 98/54182 | | 12/1998 |
| WO | WO 0045846 | * | 1/2000 |
| WO | WO 00/32600 | | 6/2000 |
| WO | WO 00/45846 | | 8/2000 |
| WO | WO/02/20521 | | 3/2002 |
| WO | WO/02/085357 | | 10/2002 |
| WO | WO 2004013137 | * | 2/2004 |
| WO | WO 2005/037832 | | 4/2005 |
| WO | WO 2005/060947 | | 7/2005 |
| WO | WO/2005/111038 | | 11/2005 |

OTHER PUBLICATIONS

Rajendra et. al, Journal of Medicinal chemistry, 1967, vol. 10 p. 510.*
Nielsen et al, Journall of Medicinal Chemistry, 2000, 43, 2217-2226.*
English translation of WO 2000045846.*
STN structure print out of WO 2000045846 document.*
Coe et al. (2005) Varenicline: An α4β2 Nicotinic Receptor Partial Agonist for Smoking Cessation, *J. Med. Chem.*, 48:3474-3477.
Lukas et al. (1999) International Union of Pharmacology. XX. Current Status of the Nomenclature for Nicotinic Acetylcholine Receptors and Their Subunits, *Pharm. Rev.*, 51(2):397-401.
Yarnell (2005) "Design of an Antismoking Pill," *Chem. & Eng. News*, 83(23): 36-37.
PCT International Search Report, mailing date Aug. 27, 2008, for PCT application PCT/US2007/023152.
Written Opinion of the International Searching Authority, mailing date Aug. 27, 2008, for PCT application PCT/US2007/023152.

* cited by examiner

*Primary Examiner* — Savitha Rao
*Assistant Examiner* — Angela Brown-Pettigrew
(74) *Attorney, Agent, or Firm* — Richard Aron Osman; Isaac Rutenberg

(57) ABSTRACT

The disclosure provides compounds capable of selectively or non-selectively modulating nicotinic acetylcholine receptors. The compounds, compositions, and methods described herein are useful, for example, in treating patients suffering from various medical conditions including pain, chemical addictions, Parkinson's disease, Alzheimer's disease, and neurodegenerative disorders. In one embodiment, the compounds comprise a 7- to 11-membered azabicyclo ring.

16 Claims, No Drawings

US 8,697,722 B2

NICOTINIC ACETYLCHOLINE RECEPTOR MODULATORS

GOVERNMENT RIGHTS

This invention was made with Government support under contract Number 1 R01 DA020811 awarded by the National Institute of Drug Abuse. The Government has certain rights in this invention.

TECHNICAL FIELD

This disclosure relates generally to compounds that modulate human neuronal nicotinic acetylcholine receptors, and more particularly relates to compounds useful in the treatment of conditions that are mediated by such receptors.

BACKGROUND

Nicotine, the active ingredient in tobacco, stimulates neuronal receptors by triggering the release of neurotransmitters such as dopamine and acetylcholine. To produce this effect, nicotine is believed to bind to one or more of a family of receptors known as nicotinic acetylcholine receptors (nAChRs).

Tobacco use is widely recognized as damaging to the health of individual users and draining on public resources. Although many addicted smokers desire to quit, dependency on the artificially high levels of neurotransmitters caused by nicotine can make smoking cessation a very difficult process. Discontinuing the intake of nicotine leads to sometimes severe physical and psychological withdrawal symptoms that may include cravings, irritability, nervousness, sleep deprivation, weight gain, and physical illness.

Therapeutic approaches to aid in smoking cessation include nicotine replacement therapy (NRT) methodologies that involve the slow delivery of controlled doses of nicotine. For the addicted smoker, maintaining a low level of nicotine in the circulation helps to address the physical and psychological withdrawal symptoms associated with smoking cessation. However, the efficacy of NRT methods is often very low.

Non-nicotine based methods of aiding smoking cessation that are under investigation include the use of anti-depressants and weight-reducing medications. Coc et al., (2005) *J. Med Chem.* 48, 3474 describes the synthesis of an azepine derivative that, like nicotine, binds to one of the nAChRs. It is hypothesized that a therapeutic agent that competitively binds to nAChRs, precluding the binding of nicotine, would thereby limit or eliminate the satisfaction that smoking provides.

Various compounds and methods have been investigated as aids for smoking cessation. For example, U.S. Pat. No. 6,964,972 describes 8-azabicylco[3.2.1]oct-2-ene and -octane derivatives which are useful for the treatment of a range of diseases or conditions or disorders characterized by decreased cholinergic function or responsive to the activity of nicotinic ACh receptor modulators.

U.S. Pat. No. 6,541,478 describes a method for treating a person for nicotine dependency by administering an opioid antagonist such as naltrexone.

U.S. Pat. No. 6,495,605 describes methods and compositions that utilize the optically pure (+)-isomer of bupropion to assist in smoking cessation, and for treating smoking and nicotine addiction.

In addition, various nAChRs have been identified as targets for drugs that aid in smoking cessation. For example, U.S. Pat. Nos. 6,951,868, 6,919,359, 6,911,543, 6,894,042, 6,858,613, 6,852,716, and 6,849620 are directed towards azabicyclic compounds that are useful in pharmaceuticals in which the α7 nAChR is known to be involved.

However, it is not well understood which of the numerous nAChRs is/are most relevant for smoking cessation. Development of competitive ligands for binding to nAChRs remains a promising area of research, and there remains a need in the art for improved therapeutic approaches to aid in smoking cessation.

Furthermore, nAChRs play an important role in regulating CNS and other physiological functions by mediating the endogenous neurotransmitter, acetylcholine. Consequently, a wide variety of conditions are associated with nAChRs and the chemicals with which they interact. Effective approaches toward treating any or all of these conditions may be achieved via drugs that target the function of nAChRs. For example, and in addition to nicotine addiction, nAChRs are associated with medical conditions such as learning disorders, eating disorders, Alzheimer's disease and other memory-impairing conditions, Parkinsons disease, and addictions to drugs such as opiates and cocaine. As with nicotine addiction, there remains a need in the art for improved therapeutic approaches to these nAChR-associated conditions.

An improved therapeutic approach to aid in the treatment of drug addictions (such as nicotine) or other medical conditions involving nAChRs might involve a compound that: (1) has a selective and high binding affinity for one or more subtype of neuronal nAChR; (2) has a low binding affinity for muscular AChRs; (3) has low toxicity in vivo; and (4) can be administered to the patient effectively and via one or more of a variety of methods.

It is an object of the present disclosure to address one or more of the aforementioned needs in the art, by providing compounds, compositions, methods of use, and methods of treatment that are directed at modulating one or more nAChR.

SUMMARY OF THE DISCLOSURE

In one embodiment, the present disclosure provides a method for modulating a nicotinic acetylcholine receptor (nAChR). The method comprises administering to a patient a therapeutically effective amount of a compound comprising a 7- to 11-membered azabicyclo ring attached to a bulk-providing moiety. The bulk-providing moiety is selected from: (i) N-heteroaryl; (ii) indolinyl-2-one; and (iii) N-substituted aryl.

In another embodiment, the disclosure provides a method for treating a patient suffering from a chemical addition. The method comprises administering to the patient a therapeutically effective amount of a compound capable of binding to a nicotinic acetylcholine receptor. The compound comprises a 7- to 11-membered azabicyclo ring attached to a bulk-providing moiety selected from: (i) N-heteroaryl; (ii) indolinyl-2-one; and (iii) N-substituted aryl.

In a further embodiment, the disclosure provides a compound comprising a 7- to 11-membered azabicyclo ring that has a bulk-providing moiety. The bulk-providing moiety is selected from: (i) N-heteroaryl; (ii) indolinyl-2-one; and (iii) N-substituted aryl, and the compound is a ligand for a nicotinic acetylcholine receptor (nAChR).

In a still further embodiment, the disclosure provides a composition comprising: (1) a compound comprising a 7- to 11-membered azabicyclo ring that has a bulk-providing moiety selected from: (i) N-heteroaryl; (ii) indolinyl-2-one; and (iii) N-substituted aryl; and (2) a pharmaceutically acceptable carrier. The compound is a ligand for a nicotinic acetylcholine receptor (nAChR).

DETAILED DESCRIPTION OF THE INVENTION

Definitions

Unless otherwise indicated, the disclosure is not limited to specific formulations, administration regimens, drug delivery devices, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an active agent" includes not only a single active agent but also a combination or mixture of two or more different active agents, reference to "a polymer" includes a single polymer as well as two or more polymers in combination or admixture, and the like.

In describing and claiming the present invention, the following terminology will be used in accordance with the definitions set out below.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinotinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

By two moieties being "connected" is intended to include instances wherein the two moieties are directly bonded to each other, as well as instances wherein a linker moiety (such as an alkylene or heteroatom) is present between the two moieties.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

Unless otherwise indicated, the terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. "Preventing" a disorder or unwanted physiological event in a patient refers specifically to the prevention of the occurrence of symptoms and/or their underlying cause, wherein the patient may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the individual, the particular beneficial agent or agents, and the like. Thus, it is not always possible to specify an exact "effective amount." However, an appropriate "effective" amount in any individual case may be determined by one of ordinary skill in the art using routine experimentation.

As used herein, and unless specifically stated otherwise, an "effective amount" of a beneficial refers to an amount covering both therapeutically effective amounts and prophylactically effective amounts.

As used herein, a "therapeutically effective amount" of an active agent refers to an amount that is effective to achieve a desired therapeutic result, and a "prophylactically effective amount" of an active agent refers to an amount that is effective to prevent an unwanted physiological condition. Therapeutically effective and prophylactically effective amounts of a given active agent will typically vary with respect to factors such as the type and severity of the disorder or disease being treated and the age, gender, and weight of the patient.

By a "pharmaceutically acceptable" component is meant a component that is not biologically or otherwise undesirable, i.e., the component may be incorporated into a pharmaceutical formulation of the disclosure and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

The term "pharmacologically active" (or simply "active"), as in a "pharmacologically active" derivative or analog, refers to a derivative or analog (e.g., a salt, ester, amide, conjugate, metabolite, isomer, fragment, etc.) having the same type of pharmacological activity as the parent compound and approximately equivalent in degree.

The term "controlled release" refers to a formulation, dosage form, or region thereof from which release of a beneficial agent is not immediate, i.e., with a "controlled release" dosage form, administration does not result in immediate release of the beneficial agent in an absorption pool. The term is used interchangeably with "nonimmediate release" as defined in *Remington: The Science and Practice of Pharmacy*, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a formulation, dosage form, or region thereof that provides for gradual release of a beneficial agent over an extended period of time, and that preferably, although not necessarily, results in substantially constant blood levels of the agent over an extended time period.

The term "naturally occurring" refers to a compound or composition that occurs in nature, regardless of whether the compound or composition has been isolated from a natural source or chemically synthesized.

As used herein, "binding" refers to the formation of a complex involving a receptor and a ligand, and "binding affinity" refers to a compound's capacity to bind to a receptor. Binding affinity may be quantified, for example, by $K_i$.

A compound may exhibit "selective" binding, by which is meant that the compound's affinity for binding to one or more particular receptor(s) is greater than the compound's affinity for binding to one other receptor, multiple other receptor, or all other receptors. For a compound that exhibits selective binding, therefore, the binding constant $K_i$ for the compound binding with one receptor is lower than the $K_i$ for the compound binding with one or more other receptor(s). For example, a compound that is selective for receptor "A" over receptor "B" will have a binding constant ratio $K_i(A)/K_i(B)$ that is less than 1/1.

In some embodiments, then, the disclosure provides compounds comprising a 7-, 8-, 9-, 10- or 11-membered azabicyclo ring. The azabicyclo ring may have any configuration, such as [2.2.1], [2.2.2], [3.2.1], [3.3.1], [3.2.2], [3.3.2], or [3.3.3], with a nitrogen atom located at any position. The azabicylco ring may be substituted or unsubstituted at any position. Multiple substituents (e.g., 2, 3, 4, 5 or more) and the linking of substituents in order to form cyclic structures are within the scope of the disclosure. The azabicyclo ring may be unsaturated. Examples of azabicyclo rings include various isomers of azabicyclo[2.2.1]heptanyl, azabicylco[3.2.1]octanyl, azabicylco[2.2.2]octanyl, azabicyclo[3.2.2]nonanyl, azabicyclo[3.3.1]nonanyl, azabicylco[3.3.2]decanyl, and azabicyclo[3.3.3]undecanyl rings, any of which may be saturated or unsaturated. Example formulae of azabicyclo ring configurations, showing only the ring atoms, are as follows:

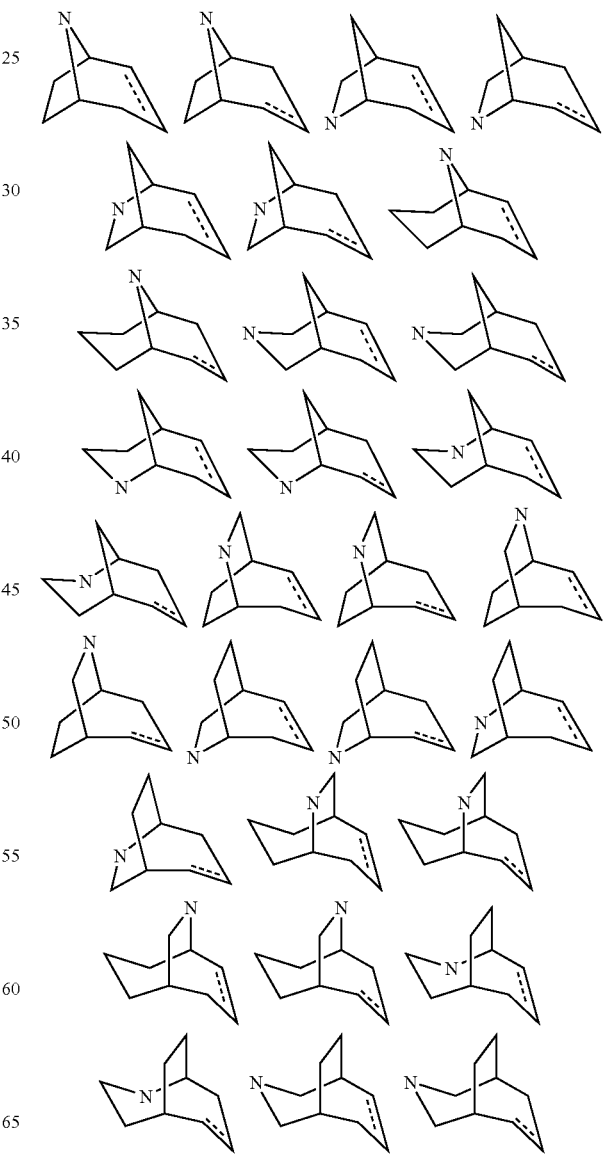

-continued

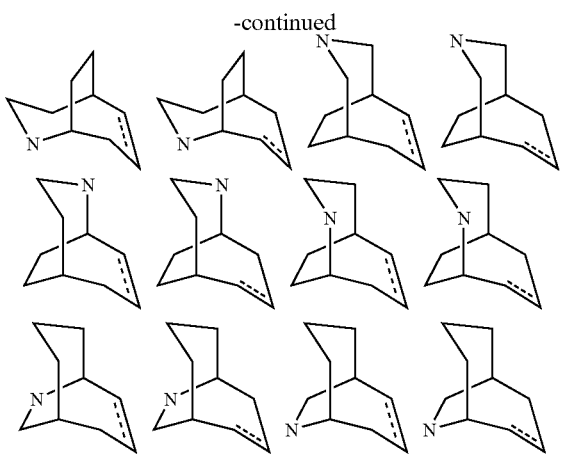

wherein the dashed lines represent optional double bonds, and each of the ring atoms may be appropriately substituted in order to satisfy the valency of the atom. It will be appreciated by one of skill in the art that azabicylco ring isomers other than those shown above are possible (including numerous 11-membered azabicylco ring isomers), and that such isomers are also within the scope of the disclosure.

When the nitrogen atom of the azabicyclo ring is not on the position of the bridgehead, it is in the form —$NR^1$—, wherein $R^1$ is selected from H, hydrocarbyl, substituted hydrocarbyl, heteroatom-containing hydrocarbyl, and substituted heteroatom-containing hydrocarbyl. Examples of $R^1$ groups include substituted or unsubstituted $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene. Further examples of $R^1$ include methyl, ethyl, benzyl, —C(O)H—, —C(O)—O—$CH_3$, —C(O)—O—$CH_2CH_3$, and —C(O)—O—$C(CH_3)_3$.

In addition to the azabicyclo ring, the compounds of the disclosure further comprise a bulk-providing moiety, and an optional linking moiety. In general, the compounds have the structure of formula (I)

(I)

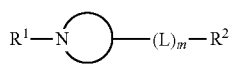

wherein, in formula (I),

represents the azabicyclo ring;
m is an integer selected from 0 or 1;
L is a linking moiety;
$R^1$ is selected from H, hydrocarbyl, substituted hydrocarbyl, heteroatom-containing hydrocarbyl, substituted heteroatom-containing hydrocarbyl, and nitrogen protecting groups; and
$R^2$ is a bulk-providing moiety.

In some embodiments of compounds having the structure of formula (I), $R^1$ is selected from H, substituted and unsubstituted $C_1$-$C_{24}$ alkyl, substituted and unsubstituted $C_1$-$C_{24}$ heteroalkyl, substituted and unsubstituted $C_5$-$C_{24}$ aryl, substituted and unsubstituted $C_5$-$C_{24}$ heteroaryl, and nitrogen protecting groups, and $R^2$ is selected from substituted and unsubstituted $C_5$-$C_{24}$ aryl, and substituted and unsubstituted $C_5$-$C_{24}$ heteroaryl. In other embodiments, $R^1$ and $R^2$ are selected from H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_5$-$C_{20}$ aryl, substituted or unsubstituted $C_5$-$C_{20}$ alkaryl, substituted or unsubstituted $C_5$-$C_{20}$ aralkyl, substituted or unsubstituted heteroatom-containing $C_1$-$C_{10}$ alkyl, substituted or unsubstituted heteroatom-containing $C_2$-$C_{10}$ alkenyl, substituted or unsubstituted heteroatom-containing $C_2$-$C_{10}$ alkynyl, substituted or unsubstituted heteroatom-containing $C_5$-$C_{20}$ aryl, substituted or unsubstituted heteroatom-containing $C_5$-$C_{20}$ alkaryl, substituted or unsubstituted heteroatom-containing $C_5$-$C_{20}$ aralkyl, and functional groups.

For example, in some embodiments, the compounds have the structure of formulae (IA), (IB), or (IC)

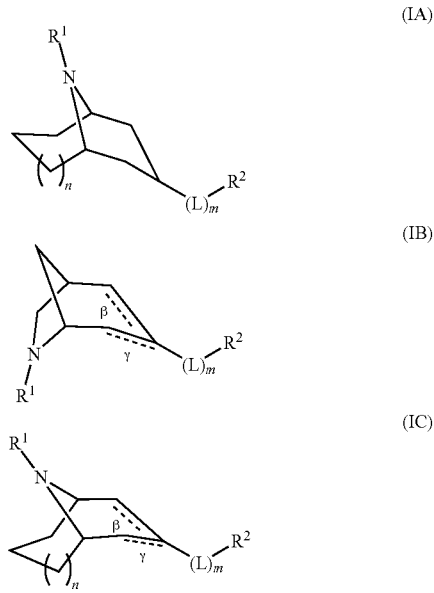

wherein, in formulae (IA), (IB), and (IC),
n is an integer selected from 0 or 1;
β and γ are optional double bonds, provided that either β or γ is present; and
m, L, $R^1$, and $R^2$ are as defined for formula (I).

In some embodiments, such as for instance compounds having the structure of formula (IA) or formula (IC), the nitrogen atom of the azabicyclo compound forms a one-atom bridge. Preferred azabicyclo compounds having nitrogen as a one-atom bridge will typically be 8- or 9-membered azabicyclo compounds.

In some embodiments, such as for instance compounds having the structure of formula (IB) or formula (IC), the azabicyclo ring contains a carbon-carbon double bond between two adjacent ring atoms.

In preferred embodiments, the bulk-providing moiety is a cyclic substituent, which may be aromatic, alicyclic, or a combination thereof, may contain 0, 1, 2, 3 or more heteroatoms, 0, 1, 2, 3, 4 or more fused rings, and may be further substituted with 0, 1, 2, 3, 4, 5 or more substituents.

The bulk-providing moiety on the azabicyclic ring may be a substituted or unsubstituted heterocyclic moiety. The heterocyclic group may be a 3-, 4-, 5-, 6-, 7-, or higher-membered cyclic group and may contain 1, 2, 3 or more heteroatoms. The heterocyclic group may be substituted with 0, 1, 2, 3, 4, 5 or more substituents, any two or more of which may be linked such that the heterocyclic group contains fused rings. Therefore, the heterocyclic group may consist of 1, 2, 3 or more rings, any of which may be aromatic or alicyclic. The azabicyclic ring may be connected to any atom within the heterocyclic group, and multiple points of attachment, such that the azabicyclic ring and the heterocyclic group form a cycle, are within the scope of the disclosure. Examples of heterocyclic groups include tetrahydropyranyl, pyridinyl, quinolinyl, isoquinolinyl, morpholinyl, azetidinyl, azetidinonyl, imidazolyl, dihydroimidazo, piperidinyl, piperizinyl, indolyl, dihydroindolyl, dihydroindolinonyl, pyrrolyl, pyrrolidinonyl, pyrrolidinyl, thienyl, benzothienyl, bipyridinyl, thiazolyl, aza-phenanthrenyl, pyrazinyl, pyrimidyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl, any of which may be further substituted.

The bulk-providing moiety may further be an aryl moiety substituted with a nitrogen-containing group (herein referred to as a "N-substituted aryl moiety"). In some embodiments, the bulk-providing moiety comprises a moiety having the structure of formula (II)

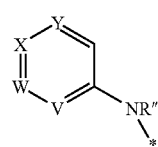

(II)

wherein, in formula (II),

V, W, X, and Y are independently selected from N and CR''', wherein R''' is selected from H, hydrocarbyl, substituted hydrocarbyl, heteroatom-containing hydrocarbyl, substituted heteroatom-containing hydrocarbyl, and functional groups;

R'' is selected from H, $C_1$-$C_{10}$ alkyl, $C_1$-$C_{10}$ acyl, $C_5$-$C_{12}$ aryl, nitrogen protecting groups, and further wherein R'' may connect with the aryl moiety to form a further cyclic structure; and

* represents the point of attachment of the bulk-providing moiety to the remainder of the compound.

In some embodiments of formula (II), the bulk-providing moiety has the structure of formula (III)

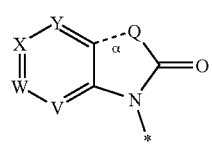

(III)

wherein, in formula (III),

V, W, X, and Y are as defined for formula (II);

α represents an optional covalent bond; and

Q is defined below.

When α is present, the bulk providing moiety is substituted or unsubstituted indolinyl-2-one. The indolinyl-2-one may be substituted with 0, 1, 2, 3, 4, 5 or more substituents at any position. Furthermore, any two or more substituents on the indolinyl-2-one may be taken together to form a cyclic structure comprising 1, 2, 3 or more rings, wherein the cyclic structure may be alicyclic, aromatic, or a combination thereof and may contain 0, 1, 2, 3 or more heteroatoms. When α is present, therefore, Q is $CR^{3a}R^{3b}$, wherein $R^{3a}$ and $R^{3b}$ are independently selected from H, hydrocarbyl, substituted hydrocarbyl, heteroatom-containing hydrocarbyl, substituted heteroatom-containing hydrocarbyl, and functional groups, or may be taken together to form a ring, or may together form =O or =S.

When α is not present, Q is selected from H, hydrocarbyl, substituted hydrocarbyl, heteroatom-containing hydrocarbyl, substituted heteroatom-containing hydrocarbyl, and functional groups.

A linking moiety is optionally present between the azabicyclo ring and the bulk-providing moiety. The linking moiety may be attached to the azabicyclo ring and/or the bulk-providing moiety at more than one location, such that the linking moiety forms a cycle with the azabicyclo ring and/or the bulk-providing moiety. In some embodiments, the linking moiety is present, and is a group selected from hydrocarbylene, substituted hydrocarbylene, heteroatom-containing hydrocarbylene, substituted heteroatom-containing hydrocarbylene, and functional groups. Examples of linking moieties include substituted or unsubstituted $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, and $C_6$-$C_{24}$ Further examples of linking moieties include substituted or unsubstituted $C_1$-$C_{20}$ heteroatom-containing alkylene, $C_2$-$C_{20}$ heteroatom-containing alkenylene, $C_2$-$C_{20}$ heteroatom-containing alkynylene, $C_5$-$C_{24}$ heteroatom-containing arylene, $C_6$-$C_{24}$ heteroatom-containing alkarylene, and $C_6$-$C_{24}$ heteroatom-containing aralkylene. Still further examples of linking groups include functional groups such as amide, imide, thio, oxa, aza, sila, and oxo. Specific examples of linking groups include —$(CH_2)_n$—, —$(OCH_2)_n$—, —$(OCH_2CH_2)_n$—, —$(OCH_2CH(CH_3))_n$—, —O—, —S—, —NR'—, —(CO)—, —(CO)—O—, —O—(CO)—, —O—(CO)—O—, —$(CH_2)_n$—NR'—, —NR'—$(CH_2)_n$—, —(CO)—NR'—, —NR'—(CO)—, —O—(CO)—NR'—, —NR'—(CO)—O—, —S—S—, —S—(CO)—, and —(CO)—S—, where n is an integer between 1 and 10, and R' is selected from H, alkyl, $C_1$-$C_{10}$ alkyl, $C_5$-$C_{12}$ aryl, acyl, and nitrogen protecting groups.

In some embodiments, the linking moiety is a nitrogen-containing moiety. As an example, the linking moiety is a nitrogen-containing moiety comprising a secondary or tertiary amine, or the nitrogen-containing moiety is an amide, or the nitrogen-containing moiety is other than an amide. In other embodiments, the linking moiety is a carbonyl-containing moiety. As an example, the linking moiety is a carbonyl-containing moiety comprising a ketone or carbonate, or the carbonyl containing moiety is an ester, or the carbonyl-containing moiety is other than an ester. It will be appreciated by those of skill in the art that, unless otherwise specified, any asymmetric moiety described herein or known in the art may be incorporated into the compounds of the disclosure in any appropriate fashion. For example, an amide linking moiety may be incorporated either as —C(=O)—NR— or —NR—C(=O), as appropriate.

In some embodiments, the linking moiety is absent such that the azabicyclo ring is directly connected to the bulk-providing moiety.

As described previously, in some embodiments, the bulk-providing moiety is an indolinyl-2-one moiety. The azabicyclo ring may be connected to the 1-position (i.e., the nitrogen atom at the 1-position) or 3-position (i.e., the carbon atom at the 3-position) of the indolinyl-2-one. Alternatively, the azabicyclo ring may be connected to a position on the aryl portion of the indolinyl-2-one. Furthermore, multiple connections between the azabicyclo ring and the indolinyl-2-one, such that the azabicylco ring and the indolinyl-2-one together form a ring, are within the scope of the disclosure.

Examples of the compounds of the disclosure comprising an azabicyclo ring substituted with indolinyl-2-one include compounds with the structure of formula (IV)

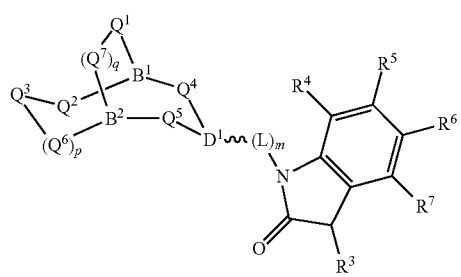
(IV)

wherein, in formula (IV):

p, q, and m are integers independently selected from zero or 1;

$B^1$, $B^2$, and $D^1$ are independently selected from N and $CR^{10}$;

$Q^1$, $Q^2$, $Q^3$, $Q^4$, $Q^5$, $Q^6$, and $Q^7$ are independently selected from $NR^1$ and $CR^8R^9$, provided that the bicyclic ring defined by $Q^1$, $Q^2$, $Q^3$, $Q^4$, $Q^5$, $Q^6$, $Q^7$, $B^1$, $B^2$, and $D^1$ contains at least one nitrogen ring atom;

L is a linker moiety selected from —NH—, —$NR^{11}$—CO—, —$NR^{11}$-$L^1$-, —CO—$NR^{11}$—, and -$L^1$-$NR^{11}$—, wherein $L^1$ is selected from substituted and unsubstituted $C_1$-$C_{12}$ alkylene, substituted and unsubstituted $C_2$-$C_{12}$ alkenylene, substituted and unsubstituted $C_2$-$C_{12}$ alkynylene, and substituted and unsubstituted $C_5$-$C_{12}$ arylene; and $R^1$ is as described previously, and $R^3$, $R^4$, $R^5$, $R^6$, $R^7$, $R^8$, $R^9$, $R^{10}$, and $R^{11}$ are independently selected from H, hydrocarbyl, substituted hydrocarbyl, substituted hydrocarbyl, and functional groups, provided that any two substituents in formula (I) may be linked to form a ring.

For example, $R^1$, $R^3$, $R^4$, $R^5$, $R^6$, $R^7$, $R^8$, $R^9$, $R^{10}$, and $R^{11}$ may be H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_5$-$C_{20}$ aryl, substituted or unsubstituted $C_5$-$C_{20}$ alkaryl, substituted or unsubstituted $C_5$-$C_{20}$ aralkyl, substituted or unsubstituted heteroatom-containing $C_1$-$C_{10}$ alkyl, substituted or unsubstituted heteroatom-containing $C_2$-$C_{10}$ alkenyl, substituted or unsubstituted heteroatom-containing $C_2$-$C_{10}$ alkynyl, substituted or unsubstituted heteroatom-containing $C_5$-$C_{20}$ aryl, substituted or unsubstituted heteroatom-containing $C_5$-$C_{20}$ alkaryl, substituted or unsubstituted heteroatom-containing $C_5$-$C_{20}$ aralkyl, or functional groups.

Examples of compounds comprising an azabicyclic ring substituted with a heteroaryl group include compounds with the structure of formula (Va) or formula (Vb)

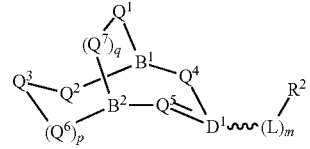
(Va)

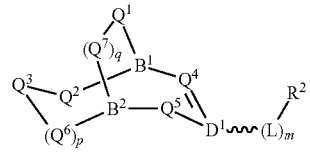
(Vb)

wherein, in formulae (Va) and (Vb), $R^2$, p, q, m, $Q^1$, $Q^2$, $Q^3$, $Q^4$, $Q^5$, $Q^6$, $Q^7$, $B^1$, $B^2$, L, and $D^1$ are as defined previously.

Examples of compounds of the disclosure include

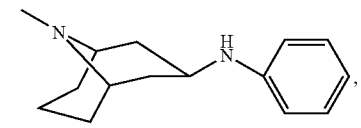
,

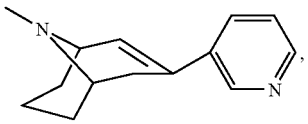
,

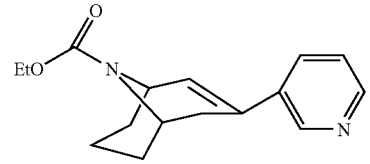
,

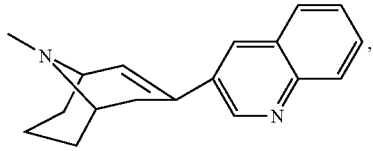
,

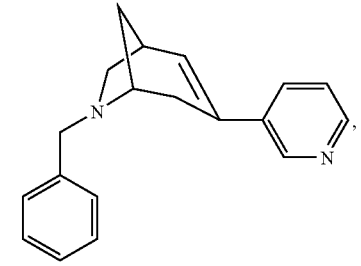
,

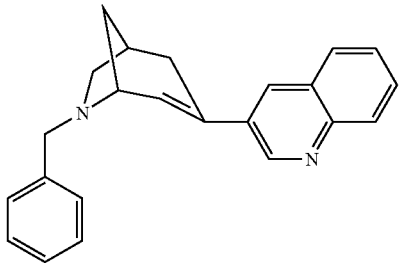

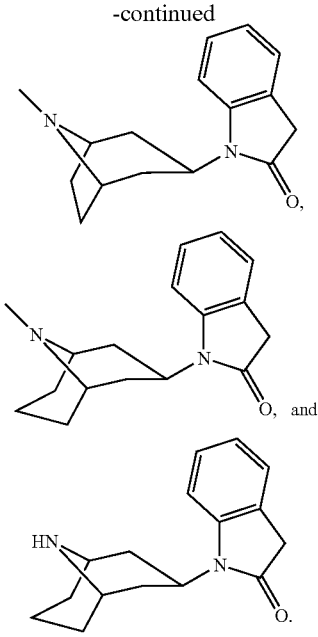

Any of the compounds described herein may be administered in the form of a salt, ester, amide, prodrug, conjugate, active metabolite, isomer, fragment, analog, or the like, provided that the salt, ester, amide, prodrug, conjugate, active metabolite, isomer, fragment, or analog is pharmaceutically acceptable and pharmacologically active in the present context. Salts, esters, amides, prodrugs, conjugates, active metabolites, isomers, fragments, and analogs of the agents may be prepared using standard procedures known to those skilled in the art of synthetic organic chemistry and described, for example, by J. March, *Advanced Organic Chemistry: Reactions, Mechanisms and Structure,* 5th Edition (New York: Wiley-Interscience, 2001).

For example, any of the compounds described herein may be in the form of a pharmaceutically acceptable salt. A pharmaceutically acceptable salt may be prepared from any pharmaceutically acceptable organic acid or base, any pharmaceutically acceptable inorganic acid or base, or combinations thereof. The acid or base used to prepare the salt may be naturally occurring.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glucamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Preparation of esters involves transformation of a carboxylic acid group via a conventional esterification reaction involving nucleophilic attack of an $RO^-$ moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Any of the compounds of the disclosure may be the active agent in a formulation as described herein. Formulations containing the compounds of the disclosure may include 1, 2, 3 or more of the compounds described herein, and may also include one or more additional active agents.

The amount of active agent in the formulation typically ranges from about 0.05 wt % to about 95 wt % based on the total weight of the formulation. For example, the amount of active agent may range from about 0.05 wt % to about 50 wt %, or from about 0.1 wt % to about 25 wt %. Alternatively, the amount of active agent in the formulation may be measured so as to achieve a desired dose, as described below.

Formulations containing the compounds of the disclosure may be presented in unit dose form or in multi-dose containers with an optional preservative to increase shelf life.

The compositions of the disclosure may be administered to the patient by any appropriate method. In general, both systemic and localized methods of administration are acceptable. It will be obvious to those skilled in the art that the selection of a method of administration will be influenced by a number of factors, such as the condition being treated, frequency of administration, dosage level, and the wants and needs of the patient. For example, certain methods may be better suited for rapid delivery of high doses of active agent, while other methods may be better suited for slow, steady delivery of active agent. Examples of methods of administration that are suitable for delivery of the compounds of the disclosure include parental and transmembrane absorption (including delivery via the digestive and respiratory tracts). Formulations suitable for delivery via these methods are well known in the art.

For example, formulations containing the compounds of the disclosure may be administered parenterally, such as via intravenous, subcutaneous, intraperitoneal, or intramuscular injection, using bolus injection and/or continuous infusion. Generally, parenteral administration employs liquid formulations.

The compositions may also be administered via the digestive tract, including orally and rectally. Examples of formulations that are appropriate for administration via the digestive tract include tablets, capsules, pastilles, chewing gum, aqueous solutions, and suppositories.

The formulations may also be administered via transmucosal administration. Transmucosal delivery includes delivery via the oral (including buccal and sublingual), nasal, vaginal, and rectal mucosal membranes. Formulations suitable for transmucosal deliver are well known in the art and include tablets, chewing gums, mouthwashes, lozenges, suppositories, gels, creams, liquids, and pastes.

The formulations may also be administered transdermally. Transdermal delivery may be accomplished using, for example, topically applied creams, liquids, pastes, gels and the like as well as what is often referred to as transdermal "patches."

The formulations may also be administered via the respiratory tract. Pulmonary delivery may be accomplished via oral or nasal inhalation, using aerosols, dry powders, liquid formulations, or the like. Aerosol inhalers and imitation cigarettes are examples of pulmonary dosage forms.

Liquid formulations include solutions, suspensions, and emulsions. For example, solutions may be aqueous solutions of the active agent and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, or other well known suspending agents. Also included are formulations of solid form which are intended to be converted, shortly before use, to liquid form.

Tablets and lozenges may comprise, for example, a flavored base such as compressed lactose, sucrose and acacia or tragacanth and an effective amount of an active agent. Pastilles generally comprise the active agent in an inert base such as gelatin and glycerine or sucrose and acacia. Mouthwashes generally comprise the active agent in a suitable liquid carrier.

For topical administration to the epidermis the chemical compound according to the disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Transdermal patches typically comprise: (1) an impermeable backing layer which may be made up of any of a wide variety of plastics or resins, e.g. aluminized polyester or polyester alone or other impermeable films; and (2) a reservoir layer comprising, for example, a compound of the disclosure in combination with mineral oil, polyisobutylene, and alcohols gelled with USP hydroxymethylcellulose. As another example, the reservoir layer may comprise acrylic-based polymer adhesives with resinous crosslinking agents which provide for diffusion of the active agent from the reservoir layer to the surface of the skin. The transdermal patch may also have a delivery rate-controlling membrane such as a microporous polypropylene disposed between the reservoir and the skin. Ethylene-vinyl acetate copolymers and other microporous membranes may also be used. Typically, an adhesive layer is provided which may comprise an adhesive formulation such as mineral oil and polyisobutylene combined with the active agent.

Other typical transdermal patches may comprise three layers: (1) an outer layer comprising a laminated polyester film; (2) a middle layer containing a rate-controlling adhesive, a structural non-woven material and the active agent; and (3) a disposable liner that must be removed prior to use. Transdermal delivery systems may also involve incorporation of highly lipid soluble carrier compounds such as dimethyl sulfoxide (DMSO), to facilitate penetration of the skin. Other carrier compounds include lanolin and glycerin.

Rectal or vaginal suppositories comprise, for example, an active agent in combination with glycerin, glycerol monopalmitate, glycerol, monostearate, hydrogenated palm kernel oil and fatty acids. Another example of a suppository formulation includes ascorbyl palmitate, silicon dioxide, white wax, and cocoa butter in combination with an effective amount of an active agent.

Nasal spray formulations may comprise a solution of active agent in physiologic saline or other pharmaceutically suitable carder liquids. Nasal spray compression pumps are also well known in the art and can be calibrated to deliver a predetermined dose of the solution.

Aerosol formulations suitable for pulmonary administration include, for example, formulations wherein the active agent is provided in a pressurized pack with a suitable propellant. Suitable propellants include chlorofluorocarbons (CFCs) such as dichlorodifluoromethane, trichlorofluoromethane, or dichlorotetrafluoroethane, carbon dioxide, or other suitable gases. The aerosol may also contain a surfactant such as lecithin. The dose of drug may be controlled by provision of a metered valve.

Dry powder suitable for pulmonary administration include, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. Unit doses for dry powder formulations may be, for example, in the form of capsules or cartridges of, e.g., gelatin, or blister packs from which the powder may be administered by means of an inhaler.

In addition to the foregoing components, it may be necessary or desirable in some cases (depending, for instance, on the particular composition or method of administration) to incorporate any of a variety of additives, e.g., components that improve drug delivery, shelf-life and patient acceptance. Suitable additives include acids, antioxidants, antimicrobials, buffers, colorants, crystal growth inhibitors, defoaming agents, dituents, emollients, fillers, flavorings, gelling agents, fragrances, lubricants, propellants, thickeners, salts, solvents, surfactants, other chemical stabilizers, or mixtures thereof. Examples of these additives can be found, for example, in M. Ash and I. Ash, *Handbook of Pharmaceutical Additives* (Hampshire, England: Gower Publishing, 1995), the contents of which are herein incorporated by reference.

Appropriate dose and regimen schedules will be apparent based on the present disclosure and on information generally available to the skilled artisan. When the compounds of the disclosure are used in the treatment of a drug addiction, achievement of the desired effects may require weeks or months of controlled, low-level administration of the formulations described herein.

The amount of active agent in formulations that contain the compounds of the disclosure may be calculated to achieve a specific dose (i.e., unit weight of active agent per unit weight of patient) of active agent. Furthermore, the treatment regimen may be designed to sustain a predetermined systemic level of active agent. For example, formulations and treatment regimen may be designed to provide an amount of active agent that ranges from about 0.001 mg/kg/day to about 100 mg/kg/day for an adult. As a further example, the amount of active agent may range from about 0.1 mg/kg/day to about 50 mg/kg/day, about 0.1 mg/kg/day to about 25 mg/kg/day, or about 1 mg/kg/day to about 10 mg/kg/day. One of skill in the art will appreciate that dosages may vary depending on a variety of factors, including method and frequency of administration, physical characteristics of the patient, level of drug addiction of the patient, duration of treatment regimen, and the severity of withdrawal symptoms that are experienced by the patient.

Treatment regimens that make use of multiple methods of administration are within the scope of the disclosure. For example, when used as smoking cessation agents, a small, steady dose of the compounds of the disclosure may be administered continuously via transdermal patch, while an additional dose can be administered as needed by the patient via chewing gum.

The compounds of the disclosure are ligands for one or more of the neuronal nicotinic acetylcholine receptors (nAChRs), a group of receptors that includes, for example, $\alpha 3\beta 4$, $\alpha 3\alpha 5\beta 4$, $\alpha 3\alpha 5\beta 2\beta 4$, $\alpha 4\beta 2$, $\alpha 4\alpha 5\beta 2$, $\alpha 7$, and $\alpha 9^*$. These receptors are described in, for example, Lukas et al. (1999) *Pharmacological Reviews* 51(2), 397-401. Therefore, the compounds of the disclosure are capable of binding to nAChRs.

The compounds of the disclosure may be competitive or noncompetitive with endogenous ligands, and may further exhibit agonistic or antagonistic activity. In addition to their ability to bind to one or more nAChRs, the compounds of the disclosure may also be either agonists or antagonists.

The compounds of the disclosure may have a high binding affinity for one or more nAChR. For example, the compounds may have binding coefficient values (i.e., $K_i$) for any of the abovementioned nAChRs that are less than about 1000, less than about 700, less than about 500, less than about 300, less than about 200, less than about 100, less than about 50, less than about 30, less than about 10, less than about 5, less than about 3, or less than about 2.

The compounds may further be selective ligands for any one or combination of the neuronal nAChRs. In some embodiments, the compounds are selective for $\alpha 3\beta 4$, $\alpha 4\beta 2$, $\alpha 7$, or any combination thereof over other nAChRs. For example, the compounds may be selective for $\alpha 3\beta 4$ and $\alpha 4\beta 2$ nAChRs over other nAChRs. As another example, the compounds are selective for the $\alpha 3\beta 4$ nAChR, and in yet another example, the compounds are selective for the $\alpha 4\beta 2$ nAChR. In some embodiments, the compounds are selective for $\alpha 3\beta 4$, $\alpha 4\beta 2$, and/or $\alpha 7$, and have a ratio $K_i(A)/K_i(B)$ (where A=$\alpha 3\beta 4$, $\alpha 4\beta 2$, or $\alpha 7$, and B=any other nAChR) that is less than 1, less than about 0.5, less than about 0.2, less than about 0.1, less than about 0.05, less than about 0.02, less than about 0.01, less than about 0.005, less than about 0.001, or less than about 0.0001.

In some embodiments, the compounds of the disclosure are useful in methods of treating patients suffering from chemical addictions. Patients with chemical addictions that may be treated with the compounds, compositions, and methods disclosed herein include patients addicted to nicotine, opioids, cocaine, and the like. The compounds may be used, for example, in aiding smoking cessation. In this example, the compounds may be used alone or in combination with other nicotine-addiction treatment methods.

In some embodiments, the compounds of the disclosure are analgesics, and are useful in the treatment of pain and in certain pain therapy regimens. In another embodiment, the compounds disclosed herein are useful in the treatment of patients suffering from Parkinson's Disease, Alzheimer's Disease, neurodegenerative disorders, and the like.

The compounds of the disclosure may be prepared using synthetic methods as exemplified in the experimental section herein, as well as standard procedures that are known to those skilled in the art of synthetic organic chemistry and used for the preparation of analogous compounds. Appropriate synthetic procedures may be found, for example, in J. March, *Advanced Organic Chemistry: Reactions, Mechanisms and Structure*, 5th Edition (New York: Wiley-Interscience, 2001). Syntheses of representative compounds are detailed in the Examples.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the disclosure has been described in conjunction with the preferred specific embodiments thereof, that the foregoing description as well as the examples that follow, are intended to illustrate and not limit the scope of the disclosure. It should be understood by those skilled in the art that various changes may be made and equivalents may be substituted without departing from the scope of the disclosure, and further that other aspects, advantages and modifications will be apparent to those skilled in the art to which the disclosure pertains.

EXAMPLES

General $^1$H and $^{13}$C NMR spectra were recorded on a Varian Gemini 300 MHz spectrometer (300 MHz and 75 MHz, respectively) and are internally referenced to chloroform at $\delta$ 7.27. Data for $^1$H NMR are reported as follows: chemical shift ($\delta$ ppm), multiplicity (s=singlet, d=doublet, t=triplet, q=quartet, m=multiplet), coupling constant (Hz), integration, and assignment. Data for $^{13}$C are reported in terms of chemical shift. IR spectra were recorded on a Perkin-Elmer 1610 spectrometer and are reported in terms of frequency of absorption (cm$^{-1}$). Mass spectra were obtained using a ThermoFinnigan LCQ Duo LC/MS/MS instrument and an electrospray ionization probe. Thin-layer chromoatgraphy was run on Analtech Uniplate silica gel TLC plates. Flash chromatography was carried out using silica gel, Merck grade 9385, 230-400 mesh. Reverse phase chromatography was carried out using C18 reverse phase silica gel, purchased from Baker. Microwave irradiation of reaction mixtures were carried out in capped vials in the Personal Chemistry Microwave Irradiator, Smith Creator.

Example 1

Synthesis of SR 16584

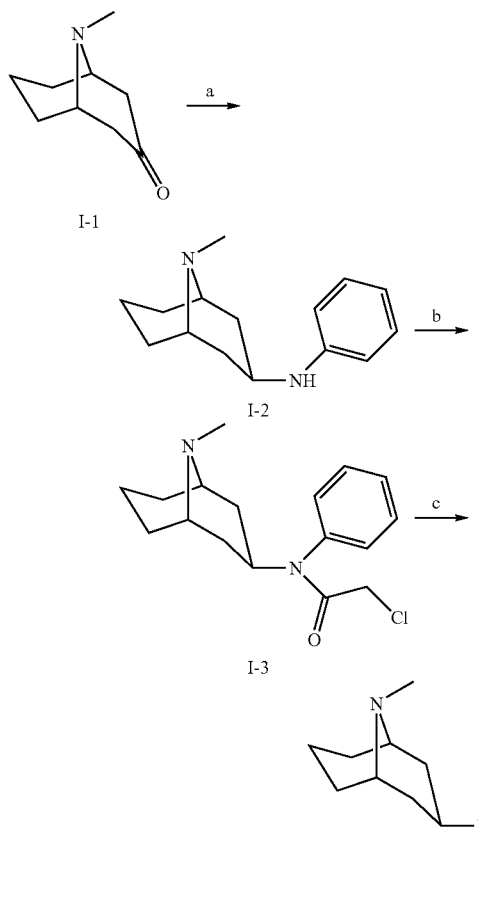

SR 16584

Reagents and reaction conditions: a. aniline, molecular sieves, toluene,reflux, sodium cyanoborohydride, methanol; b. chloroacetyl chloride, triethylamine, methylene chloride, reflux; c. aluminum chloride, 130-160° C.

Compound I-2.

A solution of I-1 (4.8 g, 31.4 mmol) and aniline (5.8 g, 5.7 mL) in benzene (25 mL) was treated with 5 Å molecular sieves (1 g) and refluxed under argon for five days, using a Dean-Stark trap filled with 3 Å molecular sieves, The mixture was cooled and filtered through Celite, evaporated to dryness and re-dissolved in methanol (20 mL). Sodium cyanoborohydride (1.97 g, 31.4 mmol) was then added and the solution was stirred under argon at room temperature 16 h. The reaction was then cooled to 5° C., acidified with dilute hydrochloric acid and the methanol was evaporated. The pH of the resulting solution was brought to 11 with potassium carbonate and the product extracted with chloroform (2×), dried (sodium sulfate) and evaporated to an oil. The mixture was purified by flash chromatography eluting with 0-8% methanol containing 5% of 28% ammonium hydroxide/methylene chloride to give 2.08 g recovered I-1 and 1.80 g product I-2 (44% based on consumed I-1).

Compound I-3.

To a solution of I-2 (609 mg, 2.66 mmol) in methylene chloride (10 mL) was added triethylamine (807 mg, 1.11 mL) followed by chloroacetyl chloride (600 mg, 423 uL) dropwise under argon. The solution was refluxed 24 h, stirred at room temperature an additional 36 h and evaporated. The mixture was purified by flash chromatography eluting with 0-6% methanol containing 5% of 28% ammonium hydroxide/methylene chloride to give I-3 as a white solid (576 mg, 71%).

SR 16584.

A mixture of I-3 (576 mg, 1.88 mmol) and aluminum chloride (1.00 g, 7.51 mmol) under argon was placed in a 160° C. oil bath and stirred for 15 min and allowed to cool to 130° C. and kept at this temperature 1.75 h. A solution of 1N sodium hydroxide (10 mL) was added and the resulting mass was sonicated to homogeneity and extracted three times with methylene chloride, dried (sodium sulfate) and evaporated to an oil. The oil was purified by flash chromatography eluting with 0-6% methanol containing 5% of 28% ammonium hydroxide/methylene chloride to give SR 16584 as an off white solid (219 mg, 43%).

Example 2

Synthesis of SR 17004

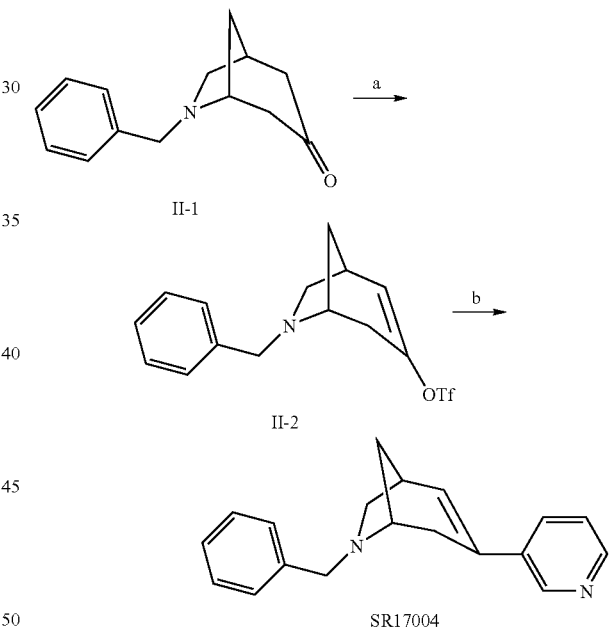

SR17004

Reagents and reaction conditions: a. NaN(TMS)$_2$, N-(5-chloro-2-pyridyl)triflimide, THF, -78° C.; b. 3-pyridineboronic acid, Pd(PPh$_3$)$_4$, dioxane, 85° C.

Compound II-1 was synthesized using reported procedures. See: Garigipati, R. S. et al., 1984, *J. Am. Chem. Soc.*, 106:7854-7860; and Pitner, J. B. et al., 1991, *J. Chem. Soc. Perkin Trans* 1 1375-1381.

Compound II-2. A solution of II-1 (1.06 g, 5.00 mmol) in THF (10 mL) was added dropwise (1 mL/min) to a solution of sodium bis(trimethylsilyl)amide [NaN(SiMe$_3$)$_2$] (7.5 mL, 1.0 M in THF, 7.5 mmol) at -78° C., and the mixture was stirred at -78° C. for 2 h. Then, a solution of N-(5-chloro-2-pyridyl) triflimide (2.9 g, 7.4 mmol) in THF (10 mL) was added in one portion at -78° C. The resultant mixture was stirred at the same temperature for 2 h, warmed to 0° C.; ether (50 mL) was added, followed by addition of saturated sodium bicarbonate (15 mL). The aqueous was separated and extracted with ether (2×25 mL). The combined organic solution was dried over potassium carbonate and evaporated to give light yellow oil, which was subjected to chromatography on silica gel, eluting with a mixture solvent of ethyl acetate (20%) and hexanes, to give two fractions; compound II-2 (0.31 g, 18%) was obtained from fraction 1 and its isomer (0.62 g, 36%) from fraction 2.

SR17004.

A mixture of II-2 (140 mg, 0.40 mmol), 3-pyridineboronic acid (55 mg, 0.45 mmol), Pd(PPh$_3$)$_4$ (23 mg, 0.02 mmol), K$_3$PO$_4$ (128 mg, 0.60 mmol), and dioxane (4 mL) was stirred at 85° C. overnight (17 h). The mixture was treated with NaOH (2 M) to strong basic (pH>12) and extracted with ethyl acetate (3×10 mL). The extract was washed with brine, dried over sodium sulfate, and evaporated to dryness. The residue was subjected to chromatography on silica gel, eluting with a mixture solvent of ethyl acetate/hexanes/methanol (5/5/1) to afford 36 mg of SR17004 (32%).

Example 3

Synthesis of SR 17026

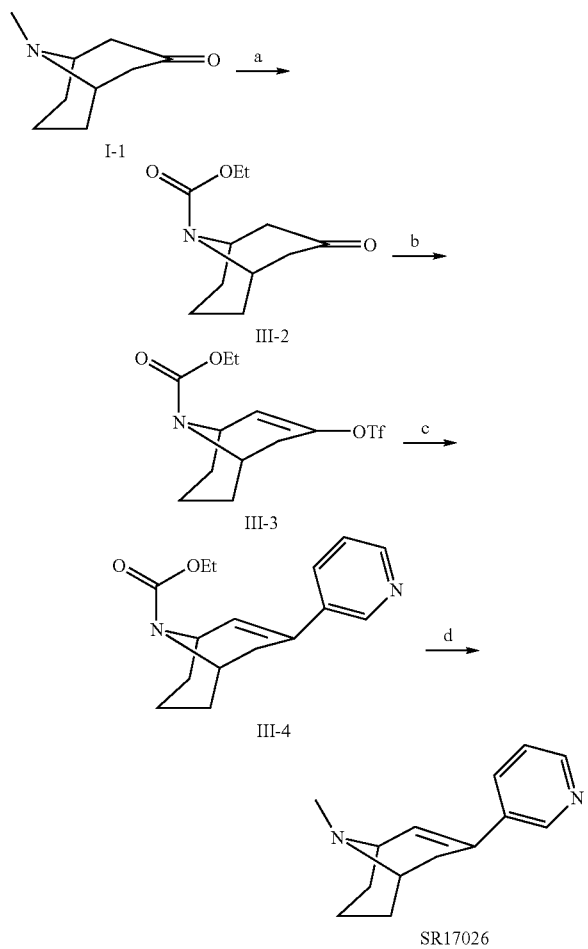

Scheme III

Reagents and reaction conditions: a. ethyl chloroformate. K$_2$CO$_3$, toluene, 90-100° C.; b. NaN(TMS)$_2$, N-(5-chloro-2-pyridyl)triflimide, THF, -78° C.; c. 3-pyridineboronic acid, Pd(PPh$_3$)$_4$, K$_3$PO$_4$, dioxane, 85° C.; d. LAH, THF.

Compound III-2.

A mixture of pseudopelletierine I-1 (3.1 g, 20 mmol), ethyl chloroformate (4.0 mL, 20 mmol), K$_2$CO$_3$ (560 mg, 4 mmol), and toluene (40 mL) was stirred at 90-100° C. for 8 h. The mixture was treated with hydrochloric acid (2 M, 30 mL) after cooled to room temperature. The aqueous phase was separated and extracted twice with ethyl acetate (30 mL). The combined organic phase was washed with saturated NaHCO$_3$ (30 mL) and brine, dried over sodium sulfate, and evaporated to brownish oil (3.8 g, 83%). A colorless material (3.5 g, 76%) was obtained after filtration through a silica gel pad, eluting with ethyl acetate/hexanes (1/1).

Compound III-3.

A solution of III-2 (1.13 g, 5.00 mmol) in THF (10 mL) was added dropwise (1 mL/min) to a solution of sodium bis(trimethylsilyl)amide [NaN(TMS)$_2$] (7.5 mL, 1.0 M in THF, 7.5 mmol) at −78° C., and the mixture was stirred at −78° C. for 2 h. Then, a solution of N-(5-chloro-2-pyridyl)triflimide (2.9 g, 7.4 mmol) in THF (10 mL) was added in one portion at −78° C. The resultant mixture was stirred at the same temperature for 2 h, warmed to 0° C.; ether (50 mL) was added, followed by addition of saturated sodium bicarbonate (15 mL). The aqueous was separated and extracted with ether (2×25 mL). The combined organic solution was dried over potassium carbonate and evaporated to give light yellow oil, which was subjected to chromatography on silica gel, eluting with a mixture solvent of ethyl acetate (20%) and hexanes, to give 0.71 g (78%) of III-3 and 0.53 g of starting material III-2.

Compound III-4.

A mixture of III-3 (343 mg, 1.00 mmol), 3-pyridineboronic acid (135 mg, 1.10 mmol), Pd(PPh$_3$)$_4$ (58 mg, 0.05 mmol), K$_3$PO$_4$ (320 mg, 1.50 mmol), and dioxane (5 mL) was stirred at 85° C. overnight (14 h). The mixture was treated with NaOH (2 M) to strong basic (pH>12) and extracted with ethyl acetate (3×10 mL). The extract was washed with brine, dried over sodium sulfate, and evaporated to dryness. The residue was subjected to chromatography on silica gel, eluting with a mixture solvent of ethyl acetate (50%) and hexanes to afford 180 mg of desired product III-4 (67%).

SR17026.

To a solution of compound III-4 (67 mg, 0.25 mmol) in THF (10 mL), was added lithium aluminum hydride solid (108 mg, 4.74 mmol). The resultant was stirred at room temperature for 30 minutes, and the excess of lithium aluminum hydride destroyed with ethyl acetate till no gas released, then water (0.5 mL) added. The mixture was filtered and the solid washed with ethyl acetate (10 mL). The filtrate and washing were combined, dried over sodium sulfate, evaporated to dryness. The residue was subjected to chromatography on silica gel, eluting with a mixture solvent of dichloromethane and methanol (20%), to afford 14 mg of desired product SR 17026 (35%).

Example 4

In Vitro Testing of Ligands

The K$_i$±SEM was determined for each compound in competition with [$^3$H]epibatidine. Compounds are tested on membranes derived from HEK cells that have been transfected with rat α3β4 and α4β2 receptors. Specific experiments are described below:

Cell Culture.

KXα3β4R2 and KXα4β2R2 cells are cultured in Dulbecco's modified Eagle's medium (DMEM), supplemented with 10% fetal bovine serum (FBS), 0.5% penicillin/streptomycin, and 0.4 mg/ml of geneticin. The cells are maintained in an atmosphere of 7.5% CO$_2$ in a humidified incubator at 37° C.

For binding assays, cells are plated on 100-mm dishes. For functional assays, the cells are seeded into 96-well collagen-coated plates (Becton Dickinson Biocoat) at a density of approximately 50,000 cells/well. Cells seeded at this density grow into a confluent monolayer in 24 to 30 h.

Binding Assays.

Cells are harvested by scraping the plates with a rubber policeman and then centrifuged at 500×g (2200 rpm) for 10 min. The cell pellet is suspended in Tris buffer, homogenized in a Polytron Homogenizer, and centrifugation repeated twice at 20,000×g (13,500 rpm) for 20 min. Cells are finally suspended in 5 ml of Tris buffer to determine their protein content. For binding, the cell membrane is incubated with the test compounds at concentrations ranging from $10^{-5}$ to $10^{-10}$ M in the presence of 0.3 nM of [$^3$H]epibatidine. After 3 h of incubation at room temperature, samples are filtered through glass fiber filters and presoaked in 0.1% polyethyleneimine (PEI) by using a Tomtec cell harvester, Filters are counted on a betaplate reader (Wallac). Nonspecific binding is determined by using 0.1 µM of the unlabeled epibatidine. Full characterization of compounds includes analysis of the data for $IC_{50}$ values and Hill coefficients by using the program PRISM. $K_i$ values will be calculated using the Cheng Prusoff transformation:

$$K_i = \frac{IC_{50}}{1 + L/K_d}$$

Where, L is radioligand concentration and $K_d$ is the binding affinity of the radioligand, as determined previously by saturation analysis.

Example 5

Binding Affinities of Various Compounds

Table 1 provides the structures of compounds that were screened for their binding affinities.

TABLE 1

Binding affinities of various compounds.

| Entry | Compound | Structure | α3β4 | α4β2 |
|---|---|---|---|---|
| 1 | Epibatidine | | 0.15 | 0.06 |
| 2 | Nicotine | | 480.69 | 11.13 |
| 3 | Cytisine | | 202.89 | 1.53 |
| 4 | Acetylcholine | | 619.63 | 37.74 |
| 5 | SR 16583 | 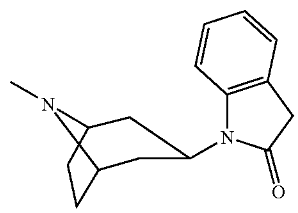 [SMILES: CN1C2CCC1CC(N1C(=O)Cc3ccccc31)C2] | 2790 | >10K |
| 6 | SR 16832 | 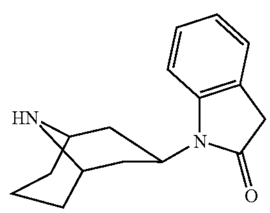 [SMILES: O=C1Cc2ccccc2N1C1CC2CCCC(C1)N2] | 421 | >10K |
| 7 | SR 16584 | 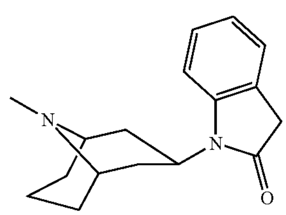 [SMILES: CN1C2CCCC1CC(N1C(=O)Cc3ccccc31)C2] | 283 | >10K |
| 8 | SR 17026 | 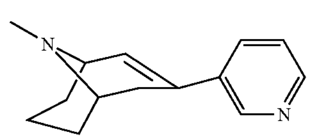 [SMILES: CN1C2C=C(c3cccnc3)CC1CCC2] | 240 | 10 |
| 9 | SR 17027 | 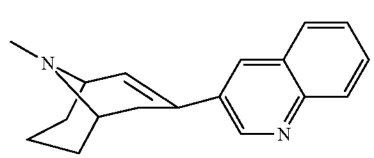 [SMILES: CN1C2C=C(c3cnc4ccccc4c3)CC1CCC2] | 2614 | 423 |

TABLE 1-continued
Binding affinities of various compounds.
| Entry | Compound | Structure | α3β4 | α4β2 |
|---|---|---|---|---|
| 10 | SR 17021 | 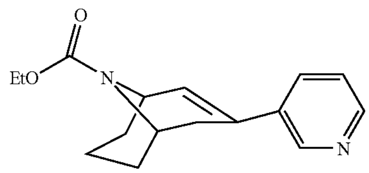 [SMILES: CCOC(=O)N1C2C=C(c3cccnc3)CC1CCC2] | >10K | >10K |
| 11 | SR 17011 | 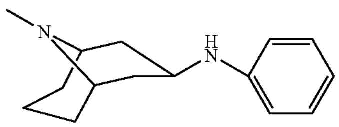 [SMILES: CN1C2CCCC1CC(Nc1ccccc1)C2] | 826 | >10K |
| 12 | SR 17004 | 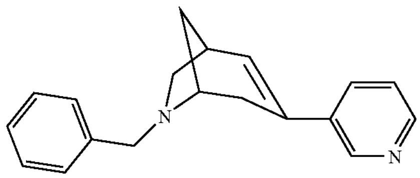 [SMILES: C1=C(c2cccnc2)CC2CC1CN2Cc1ccccc1] | 194 | 1.95 |
| 13 | SR 17015 | 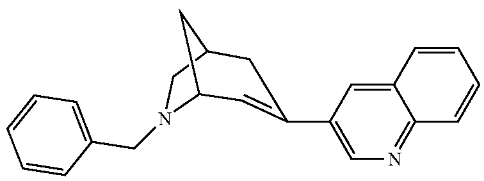 [SMILES: C1=C(c2cnc3ccccc3c2)CC2CC1N(Cc1ccccc1)C2] | 2477 | 29 |
The invention claimed is:
1. A compound having a structure selected from the group consisting of:
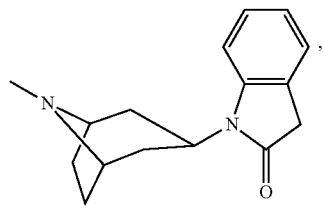 [SMILES: CN1C2CCC1CC(N1C(=O)Cc3ccccc31)C2]
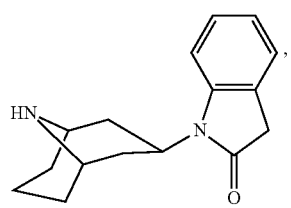
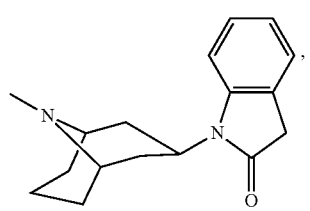
-continued
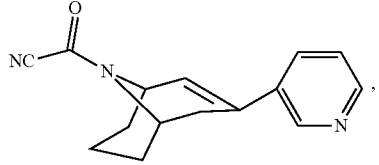
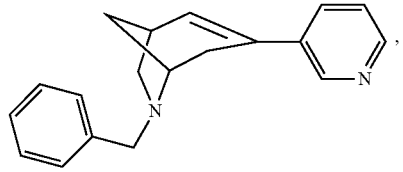
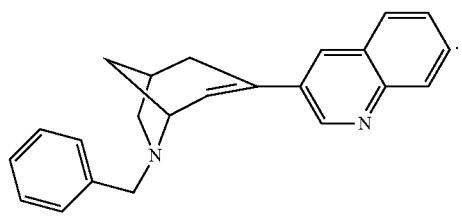
and 2. A compound of claim 1 having the structure:

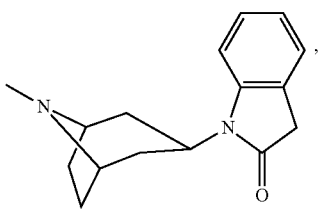

or a pharmaceutically-acceptable salt thereof.

3. A compound of claim 1 having the structure:

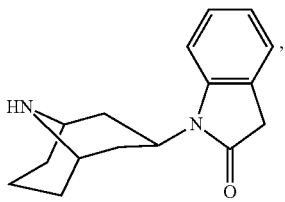 [SMILES: O=C1Cc2ccccc2N1C1CC2CCCC(C1)N2]

or a pharmaceutically-acceptable salt thereof.

4. A compound of claim 1 having the structure:

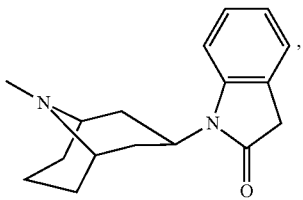 [SMILES: CN1C2CCCC1CC(N1C(=O)Cc3ccccc31)C2]

or a pharmaceutically-acceptable salt thereof.

5. A compound of claim 1 having the structure:

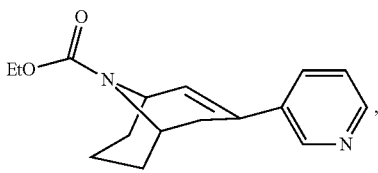 [SMILES: CCOC(=O)N1C2C=C(c3cccnc3)CC1CCC2]

or a pharmaceutically-acceptable salt thereof.

6. A compound of claim 1 having the structure:

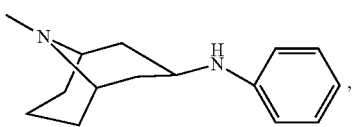

or a pharmaceutically-acceptable salt thereof.

7. A compound of claim 1 having the structure:

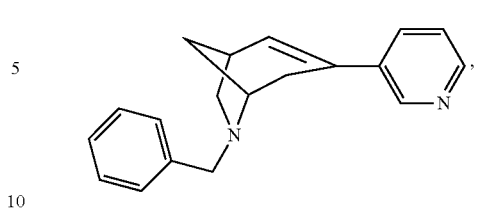

or a pharmaceutically-acceptable salt thereof.

8. A compound of claim 1 having the structure:

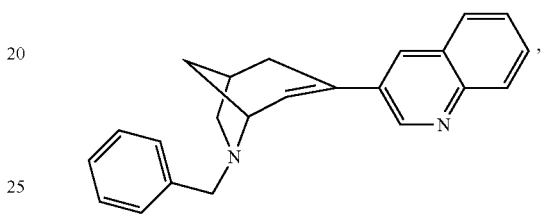

or a pharmaceutically-acceptable salt thereof.

9. A pharmaceutical composition comprising a compound of claim 1 and a pharmaceutically-acceptable carrier, in unit dosage form.

10. A pharmaceutical composition comprising a compound of claim 2 and a pharmaceutically-acceptable carrier, in unit dosage form.

11. A pharmaceutical composition comprising a compound of claim 3 and a pharmaceutically-acceptable carrier, in unit dosage form.

12. A pharmaceutical composition comprising a compound of claim 4 and a pharmaceutically-acceptable carrier, in unit dosage form.

13. A pharmaceutical composition comprising a compound of claim 5 and a pharmaceutically-acceptable carrier, in unit dosage form.

14. A pharmaceutical composition comprising a compound of claim 6 and a pharmaceutically-acceptable carrier, in unit dosage form.

15. A pharmaceutical composition comprising a compound of claim 7 and a pharmaceutically-acceptable carrier, in unit dosage form.

16. A pharmaceutical composition comprising a compound of claim 8 and a pharmaceutically-acceptable carrier, in unit dosage form.

* * * * *